(12) United States Patent
Amino et al.

(10) Patent No.: US 6,939,987 B2
(45) Date of Patent: Sep. 6, 2005

(54) METHOD FOR PRODUCING ASPARTAME DERIVATIVE, METHOD FOR PURIFYING THE SAME, CRYSTALS THEREOF AND USES OF THE SAME

(75) Inventors: Yusuke Amino, Kawasaki (JP); Kazuko Yuzawa, Kawasaki (JP); Tadashi Takemoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/656,228

(22) Filed: Sep. 8, 2003

(65) Prior Publication Data

US 2004/0049066 A1 Mar. 11, 2004

Related U.S. Application Data

(63) Continuation of application No. 10/091,500, filed on Mar. 7, 2002, which is a continuation of application No. PCT/JP00/05665, filed on Aug. 23, 2000.

(30) Foreign Application Priority Data

Sep. 7, 1999 (JP) ............................................ 11-253498

(51) Int. Cl.$^7$ ............................................ C07C 229/00
(52) U.S. Cl. ...................................................... 560/40
(58) Field of Search ............................................ 560/40

(56) References Cited

U.S. PATENT DOCUMENTS 5,480,668 A * 1/1996 Nofre et al. ................. 426/548
5,510,508 A * 4/1996 Claude et al. ................. 560/41
6,077,962 A   6/2000 Prakash et al.
6,548,096 B1  4/2003 Amino et al.
6,630,191 B1  10/2003 Amino et al.
6,649,784 B2  11/2003 Amino et al.

FOREIGN PATENT DOCUMENTS

WO  WO 99/52937   10/1999
WO  WO 00/00508   1/2000
WO  WO 00/17230   3/2000

OTHER PUBLICATIONS

S. Nishimura, "Handbook of Heterogeneous Catalytic Hydrogenation for Organic Synthesis", John Wiley & Sons, NY, pp. 178–185, 2001.

T. Fukuda, "Nippon Kagaku Zasshi", vol. 83, pp. 1126–1129, 1962.

* cited by examiner

Primary Examiner—Paul A. Zucker
(74) Attorney, Agent, or Firm—Oblon, Spivak, McClelland, Maier & Neustadt, P.C.

(57) ABSTRACT

N-[N-[3-(3-methoxy-4-hydroxyphenyl)propyl]-L-α-aspartyl]-L-phenylalanine 1-methyl ester is prepared by a process comprising:

subjecting Aspartame and 3-(3-methoxy-4-hydroxyphenyl)propionaldehyde or derivatives thereof to reductive alkylation in a solvent to produce N-[N-[3-(3-methoxy-4-hydroxyphenyl)propyl]-L-α-aspartyl]-L-phenylalanine 1-methyl ester; and crystallizing said compound.

23 Claims, 1 Drawing Sheet

[Figure 1]
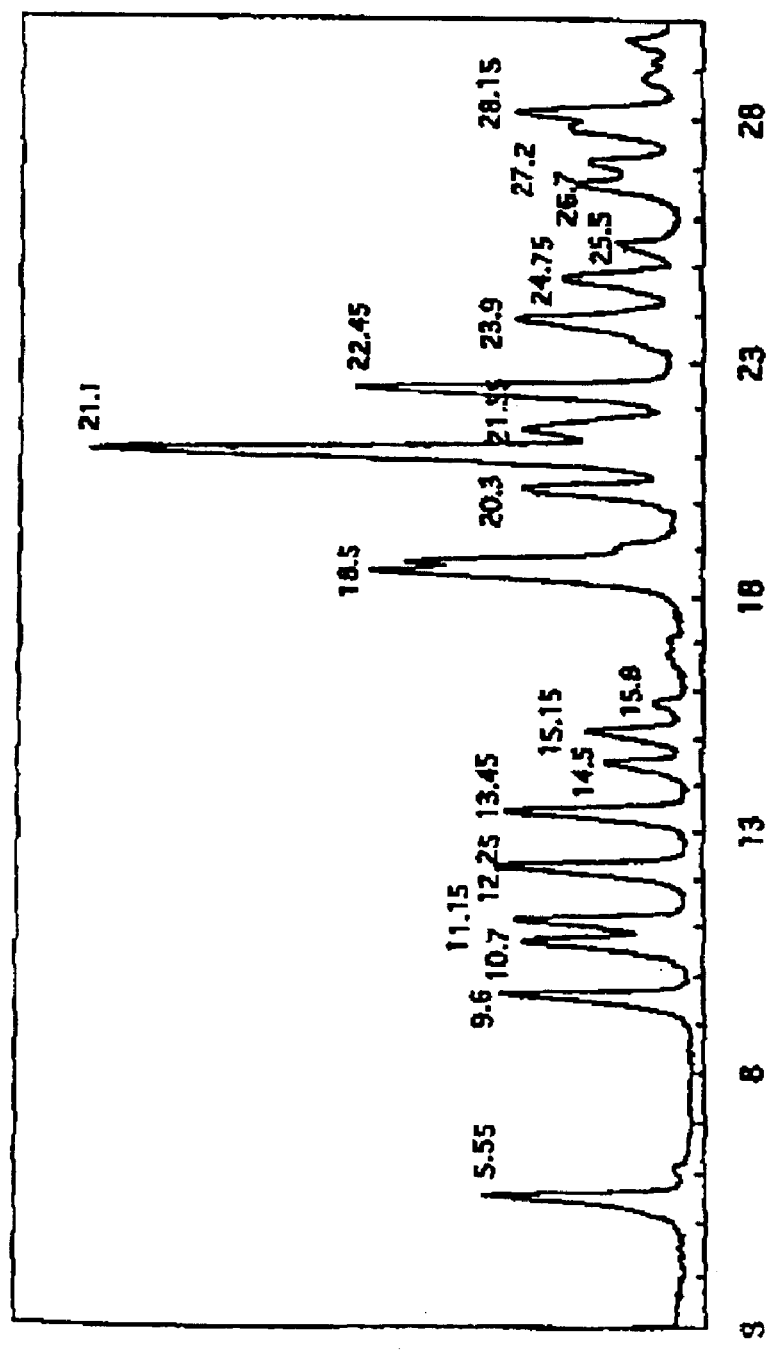

METHOD FOR PRODUCING ASPARTAME DERIVATIVE, METHOD FOR PURIFYING THE SAME, CRYSTALS THEREOF AND USES OF THE SAME

CROSS-REFERENCE TO RELATED APPLICATIONS

This application is a continuation of U.S. application Ser. No. 10/091,500, filed Mar. 7, 2002, which is a continuation application of PCT International Application No. PCT/JP00/05665, filed Aug. 23, 2000, which are incorporated herein by reference in their entirety.

BACKGROUND OF THE INVENTION

1. Field of the Invention

The present invention relates to a method for producing N-[N-[3-(3-methoxy-4-hydroxyphenyl)propyl]-L-α-aspartyl]-L-phenylalanine 1-methyl ester from Aspartame, which compound is useful as a sweetener, to a method for purifying the prepared derivative, in particular, to a method for crystallizing N-[N-[3-(3-methoxy-4-hydroxyphenyl)propyl]-L-α-aspartyl]-L-phenylalanine 1-methyl ester, to crystals of derivative which are obtained or can be obtained in these methods, to a sweetener and to other products containing the crystals of the derivative, and the like.

2. Description of the Background

In recent years, eating habits of many have improved to a high level. In this regard, the obesity of individuals which results from excessive sugar intake and the diseases which result from obesity are important health issues. Accordingly, the development of low-calorie sweetener (sweetening agent), which replaces sugar, has been in demand. A sweetener that is widely used presently Aspartame. This substance has a high level of safety and an excellent quality of sweetness. However, Aspartame presents problems of stability. International Patent Publication WO94/11391 discloses that compounds (derivatives of Aspartame) in which an alkyl group is introduced onto the amino group of aspartic acid, which constitutes Aspartame have been studied as one approach to slightly improve the stability of Aspartame and to improve its sweetening potency. Of the compounds disclosed in this publication, N-[N-(3,3-dimethylbutyl)-L-α-aspartyl]-L-phenylalanine 1-methyl ester exhibits the most excellent sweetening potency. The sweetening potency of this compound is reported to be 10000 times that of sucrose. One method employed for producing this compound is the reductive alkylation of Aspartame with sodium cyanoborohydride in the presence of 3,3-dimethylbutylaldehyde in methanol (see French Patent Publication FR2697844.). Another method of reductive alkylation is the reduction of Aspartame with hydrogen in the presence of 3,3-dimethylbutylaldehyde in the presence of platinum on carbon as a catalyst at a pH of 4.5 to 5.0 in a mixed solvent of water-methanol (see the International Patent Publication WO95/30689.). Still another of reductive alkylation is reduction of Aspartame under 0.2 MPa of hydrogen pressure in the presence of 3,3-dimethylbutylaldehyde in the presence of palladium on carbon catalyst in methanol (see U.S. Pat. No. 5,728,862). However, with regard to other Aspartame derivatives, for example, N-[N-[3-(3-methoxy-4-hydroxyphenyl)propyl]-L-α-aspartyl]-L-phenylalanine 1-methyl ester, where the sweetening potency is reported to be 2500 times that of sucrose, the various physico-chemical data are not disclosed. Moreover, there are no operational examples which should show what is used as a starting material; nor is there any disclosure of how the synthesis is conducted. Other derivatives are also not described concretely. Accordingly, a method for producing practically and industrially the compound, including a method for purifying the same, has not been studied.

SUMMARY OF THE INVENTION

Accordingly, one object of the present invention is to provide an industrially favorable method for producing N-[N-[3-(3-methoxy-4-hydroxyphenyl) propyl]-L-α-aspartyl]-L-phenylalanine 1-methyl ester, and in particular, to a method of obtaining the compound in high purity, such as in crystalline form or the like, from the reaction product or the like, and to a method for purifying the compound.

Briefly, this object and other objects of the present invention as hereinafter will become more readily apparent can be attained by an industrial method for producing N-[N-[3-(3-methoxy-4-hydroxyphenyl)propyl]-L-α-aspartyl]-L-phenylalanine 1-methyl ester of the following formula (1):

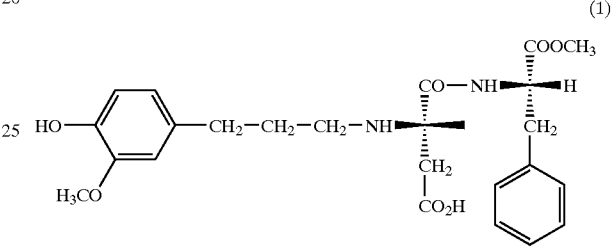

comprising:

subjecting Aspartame and 3-(3-methoxy-4-hydroxyphenyl)propionaldehyde or derivatives thereof to reductive alkylation in a solvent to produce N-[N-[3-(3-methoxy-4-hydroxyphenyl)propyl]-L-α-aspartyl]-L-phenylalanine 1-methyl ester; and crystallizing said compound.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a figure of a powder X-ray (CuKα ray) analysis pattern obtained in Example 16. The axis of abscissas: diffraction angle (2δ).

DETAILED DESCRIPTION OF THE PREFERRED EMBODIMENTS

In order to solve the problem discussed above, a study has been conducted on a method for producing N-[N-[3-(3-methoxy-4-hydroxyphenyl) propyl]-L-α-aspartyl]-L-phenylalanine 1-methyl ester (hereinafter "the object compound of the present invention", or simply "the object compound") by reductive alkylation of Aspartame and by reaction with 3-(3-methoxy-4-hydroxyphenyl) propionaldehyde, which can be easily obtained. Investigation into methods of purification of the product compound has been conducted which methods include a method of crystallization of the compound from the reaction product, and also to methods of separating the object compound in the form of a highly pure crystalline product. Further, it has now been found that the present compound can be used as a sweetener and in addition can be used stably when it is added to a product in need of a sweet taste.

With respect to the process of synthesis, it has been found that, firstly, when 3-(3-methoxy-4-hydroxyphenyl)-2-propenylaldehyde (4-hydroxy-3-methoxycinnamaldehyde, coniferyl aldehyde, Aldrich Co.), sold on the market as a reagent, or a derivative thereof in which the hydroxyl group is protected with a protecting group, such as benzyl or the like, for example, 3-(3-methoxy-4-benzyloxyphenyl)-2-propenylaldehyde, is subjected to reduction in the presence of palladium on carbon as catalyst, the compound is converted into 3-(3-methoxy-4-hydroxyphenyl) propanol, whereby approximately 90% of 3-(3-methoxy-4-hydroxyphenyl)-2-propenylaldehyde or its derivative is reduced to the alcohol. Further, these reactions have been studied under various conditions in the presence of Aspartame, and as a result, the conditions have been found by which the object compound can be obtained at approximately 50% of reaction yield.

It has also been found that when 3-(3-methoxy-4-hydroxyphenyl) propionaldehyde or 3-(3-methoxy-4-benzyloxyphenyl) propionaldehyde, wherein the double bond in the above aldehyde compounds is selectively reduced in advance, is used for the reaction, said object compound is obtained in yields of not less than 70% with little by-product formation.

With respect to a search for a method of purification to remove impurities, such as unreacted raw materials, by-products and the like, a method has now been found which makes use of the difference in solubility between the object compound, and unreacted raw materials and by-products in various solvents, and have developed a method for selectively crystallizing only unreacted Aspartame in order to separate the material from other compounds, as well as a method for extraction by distributing the object compound in the aqueous layer and other compounds in the organic solvent when practicing extraction through the distribution operation with two layers in a water-organic solvent.

Another most important point is that by studying various aspects including crystallization solvents (the solvents used for crystallization) for the object compound, finding the range of an appropriate solvent as the solvent for crystallization, and selecting an appropriate and concrete solvent used for crystallization in compliance with the material to be purified, success has now been realized in effectively separating (taking-up) the compound in the crystalline form for the first time, and this success has made industrial production possible. Furthermore, the present inventors have found that the crystalline product obtained can be stably as a sweetener, particularly for food and drink which require a sweet taste, and also other uses for the sweetener.

Aspects of the present invention include a method for producing the object compound, a method for purifying the same, crystals thereof, a sweetener, a product containing the same to impart a sweet taste, and the like.

(i) A method for producing N-[N-[3-(3-methoxy-4-hydroxyphenyl)propyl]-L-α-aspartyl]-L-phenylalanine 1-methyl ester is characterized by the fact that, for the reaction solution obtained after subjecting Aspartame and 3-(3-methoxy-4-hydroxyphenyl) propionaldehyde or its derivative to reductive alkylation in a solvent to produce the compound: N-[N-[3-(3-methoxy-4-hydroxyphenyl) propyl]-L-α-aspartyl]-L-phenylalanine 1-methyl ester, a process for crystallization of the compound is conducted, after separating the solvent therefrom in case of necessity, and in particular preferably, the process is conducted by at least one of following methods:

a. crystallization with a solvent for crystallization, such as crystallization with concentration, crystallization with substitution of solvent and the like;

b. crystallization after extraction with water; and c. crystallization after the separation of Aspartame, to crystallize the object compound.

All methods for producing the object compound (as crystals) comprise at least the process for producing and the process for crystallizing (at least one method of steps a. to c. described above) the object compound described above. Accordingly, insofar as the objectives of the present invention are not obstructed, other various pretreatments, after-treatments and/or other processes necessary for purification may be incorporated in the method, and any one of these are included in the method for producing the object compound in the present invention.

(ii) A method of purifying N-[N-[3-(3-methoxy-4-hydroxyphenyl)propyl]-L-α-aspartyl]-L-phenylalanine 1-methyl ester is characterized by subjecting N-[N-[3-(3-methoxy-4-hydroxyphenyl) propyl]-L-α-aspartyl]-L-phenylalanine 1-methyl ester comprising at least one of Aspartame, peptide derivative (other than the object compound in the present invention), amino acid, amino acid derivative, aldehyde, acetal and alcohol derivative as impurity to a process for crystallization of the object compound. The method embodies at least any one of the following methods:

a. crystallization with a solvent used for crystallization, such as crystallization with concentration, crystallization with substitution of solvent or the like;

b. crystallization after extraction with water; and c. crystallization after a process for separating Aspartame.

This method for purification is characterized by a purification (production) of the object compound, which comprises conducting at least the process for crystallizing the object compound described above (at least one method of steps a. to c. described above) for purification of the above object compound. Accordingly, all methods for purification which incorporate such a process for crystallization are included in a method for purification of the present invention. Therefore, so that the objectives of the present invention are not obstructed, other various pretreatments, after-treatments and/or other processes necessary for purification may be added thereto, and all of these are included in the method for purification of the present invention.

(iii) Novel crystals thereof which are obtained or can be obtained as described above are an aspect of the invention.

(iv) Another aspect of the invention is a sweetener in the form of crystals as described above, or a product, wherein the crystals are incorporated in a food and drink, which is to be sweetened, or the like.

(v) In order to obtain the crystals of the object compound by separation, or to purify the same, the solvent used in a process for crystallization, should be at least one solvent selected from the group consisting of alcohols (consisting of one kind of alcohol or not less than two different alcohols), such as methanol, ethanol, isopropanol and the like, tetrahydrofuran, acetonitrile, toluene, ether, acetone, acetic acid and acetic acid esters (consisting of one kind of acetic acid ester or not less than two different acetate esters), such as ethyl acetate, isopropyl acetate or the like, or a mixed solvent of at least one of these organic solvents with water (hereinafter, "the solvent used for crystallization of the object compound"). Furthermore, with regard to the mixed solvent used here, a homogeneous solvent is preferably used. However, a heterogeneous solvent can be also used.

Hereinafter, embodiments for conducting the method aspects of the present invention are explained.

(Method for Producing the Object Compound)

In order to produce N-[N-[3-(3-methoxy-4-hydroxyphenyl)propyl]-L-α-aspartyl]-L-phenylalanine 1-methyl ester, firstly, Aspartame and 3-(3-methoxy-4-hydroxyphenyl) propionaldehyde or a derivative thereof are subjected to a reductive alkylation reaction in a solvent, which can dissolve these materials, for example, an organic solvent (a singular solvent consisting of one kind of solvent or mixed solvents) or a mixed solvent of at least one solvent of these organic solvents with water. Preferably, at that time, the reaction is conducted under hydrogen in the presence of catalyst for reductive alkylation, for example, a catalyst for hydrogenation, and more preferably, the reductive alkylation reaction is conducted under a favorable or effective reaction temperature and pressure to produce N-[N-[3-(3-methoxy-4-hydroxyphenyl)propyl]-L-α-aspartyl]-L-phenylalanine 1-methyl ester, which is the object compound, and subsequently, subjecting the product to crystallization, followed by separation of the crystals of the object compound.

In the instance that an insoluble material, for example, insoluble catalyst which exists when the catalyst has been used, or the like, exists in the reaction solution obtained, it is removed whenever necessary. The insoluble material can be easily removed from the reaction solution by filtration or the like.

In the instance the process for crystallization is conducted with the reaction solution thus obtained, the object compound is crystallized from the solvent used for crystallization of the object compound described above. For example, in the case where the object compound is dissolved in the solvent used for crystallization of the object compound described above, by subjecting it to a process for crystallization by concentration, or independent to the fact whether a solvent in the solution may contain the solvent used for crystallization of the object compound described above or not, by substituting said solvent used for crystallizing the object compound (the solvent used for crystallization of the object compound), for example, the organic solvent described above (a singular solvent consisting of one kind of solvent or a mixed solvent consisting of plural solvents) or a mixed solvent of at least one solvent of these organic solvents with water, for the solvent, which was used at the reaction, the object compound can be easily crystallized therefrom. Or, the object compound can also be crystallized after extraction with water. For example, after concentration of the reaction solution, by forming layers which separate in the reaction solution with the use of organic solvent(s), which can not be mixed with water homogeneously, and water added thereto, the object compound is extracted in the aqueous layer, and further, by substituting an appropriate solvent used for crystallization (the solvent used for crystallization of the object compound described above) for the solvent therein, for example, by changing the water to the organic solvent(s) or a mixed solvent of the organic solvent(s) with water described above, the object compound can be crystallized therefrom.

On the other hand, in the method of crystallization described above, a process for separating Aspartame in advance is employed profitably in conjunction with the process for crystallization of the object compound conducted thereafter. For example, after Aspartame, which is precipitated when an appropriate organic solvent is substituted for the reaction solution solvent obtained in the above, is removed by filtration, from the solution thus obtained, the object compound is profitably crystallized.

In the reaction with Aspartame as described above, 3-(3-methoxy-4-hydroxyphenyl) propionaldehyde or a derivative thereof can be used. Suitable derivative preferably include 3-(3-methoxy-4-hydroxyphenyl)-2-propenylaldehyde, 3-(3-methoxy-4-protectedhydroxyphenyl) propionaldehyde, and 3-(3-methoxy-4-protectedhydroxyphenyl)-2-propenylaldehyde, and the acetals derived therefrom. For the protecting group of the hydroxyl group, benzyl, p-methoxybenzyl, p-nitrobenzyl or the like can be cited.

In the reductive alkylation reaction as described above, the catalyst used for the reductive alkylation reaction can be used. In this case, in a typical example, a hydrogenation catalyst, such as a palladium, platinum or rhodium based catalyst may be used.

The solvent which is used for the reductive alkylation reaction, is a solvent, which dissolves the starting materials. Suitable solvents include at least one solvent selected from the group consisting of alcohol(s) (containing an alcohol consisting of one kind of alcohol or not less than two kinds of alcohols), such as methanol, ethanol, isopropanol and the like, tetrahydrofuran, acetonitrile, toluene, acetic acid, and acetic acid ester(s) (one acetate ester or a mixture of not less than two acetate esters), such as ethyl acetate, isopropyl acetate and the like, or a mixed solvent of at least one solvent of these organic solvents with water (hereinafter, called "the solvent for the reductive alkylation reaction").

The reaction described above can be conducted by hydrogenation at a hydrogen pressure of 0.1 to 1.0 MPa or so.

With regard to the reaction temperature, a condition appropriate for the reductive alkylation reaction can be selected. However, the reaction temperature can be preferably selected within a range of 15 to 50° C. or so, and the reaction time can be preferably selected within a range of 2 to 48 hours or so, to suppress side reactions and to promote the reaction as objective.

For the molar ratio of Aspartame to 3-(3-methoxy-4-hydroxyphenyl)propionaldehyde or its derivative used for starting materials in the reaction described above, a range of 0.5 to 2 moles or so of Aspartame to 1 mole of the latter can be preferably used for the reaction.

The pH of the above reaction solvent is preferably selected within a range of 4.0 to 6.5 or so to promote the reaction.

Furthermore, for 3-(3-methoxy-4-hydroxyphenyl) propionaldehyde or its derivative to react with Aspartame, the compound can be separately (additionally) produced for use. In this case, after conducting the process for producing the compound in advance, the aldehyde or the like in the solution thus obtained as such without further treatment or the crude product obtained therefrom can be reacted with Aspartame described above. In the process, 3-(3-methoxy-4-hydroxyphenyl)-2-propenylaldehyde or its acetal, wherein the hydroxyl group may be protected, the double bond of the reactant is reduced to produce a derivative, and after this reaction, successively, the aldehyde or the like in the solution thus obtained as such without further treatment or the crude product obtained therefrom can be reacted with Aspartame. The derivative obtained is 3-(3-methoxy-4-hydroxyphenyl) propionaldehyde or its derivative, and when the process for reduction is conducted with a reductant (reducing agent), preferably, a rhodium based catalyst or the like, such as rhodium alumina catalyst and the like, the double bond is selectively reduced. Accordingly, such a reductant is preferably used. At that time, in case where the hydroxyl group is protected, such as 3-(3-methoxy-4- protectedhydroxyphenyl)-2-propenylaldehyde and the like, is used as a starting material, the protecting group in the hydroxyl group can be also removed at a time by selecting the catalyst used or by other conditions.

Subsequently, in the instance where the aldehyde or the like in the solution thus obtained as such without further treatment or the crude product obtained therefrom can be reacted with Aspartame described above, the above explanation can be applied thereto in the same manner. In case catalysts are used in the reduction reaction and the reductive alkylation reaction described above, an identical catalyst (for example, rhodium alumina catalyst is used for both of the reduction catalyst and the catalyst for the reductive alkylation) may be used therefor, and a catalyst preferred for each reaction (for example, rhodium alumina catalyst is used for the reduction catalyst and palladium carbon catalyst is used for the catalyst for the reductive alkylation) can be also used therefor respectively.

In the instance where two kinds of catalysts are used, and in addition, in the instance where, after the preceding process for reduction, successively, the reductive alkylation reaction is conducted, the reductant, which has been used in the preceding process, may be separated, or the reductant may not be separated, and thereby the reductant may also exist in the latter reaction system.

With regard to the process for crystallization in the present invention, details thereof are described as follows. However, a process for crystallization with various solvents may be utilized.

In the present invention, crystallization with concentration can be conducted with a solvent, which has been used in the reaction described above. This method is extremely easy.

(Method for Purifying the Object Compound)

When N-[N-[3-(3-methoxy-4-hydroxyphenyl)propyl]-L-α-aspartyl]-L-phenylalanine 1-methyl ester comprising at least one of Aspartame, a peptide derivative (other than the object compound), amino acid, amino acid derivative, aldehyde, acetal and alcohol derivative as impurities is purified, the material to be purified, which is described above, is in the solution form, solid form or in an intermediate stage between the solution and solid forms. However, as the process in common among them, the object compound is purified by separation after crystallization by using the solvent used for crystallization of the object compound described above. Further, in case of necessity, Aspartame, which is impurity, and the like can be separated in advance, and after extraction with water, the object compound can be also separated after crystallization.

Any one of Aspartame, a peptide derivative, an amino acid, an amino acid derivative, an aldehyde, an acetal and an alcohol derivative, which are impurities that should be removed by this method for purification, are used as a starting material in a production reaction for obtaining the object compound or the like, is a by-product in the reaction resulting from isomerization or the like.

Examples of the peptide derivative, which is an impurity, are the derivatives obtained from isomerization of Aspartame, dialkylation of Aspartame or the like during the reaction containing Aspartame, for example, (R)-aspartyl derivative, β-aspartyl derivative, dialkyl derivative and the like, which are the derivatives of Aspartame different from the object compound.

For the aldehyde and acetal, which are impurities which arise during production, examples include:
3-(3-methoxy-4-hydroxyphenyl) propionaldehyde,
3-(3-methoxy-4-hydroxyphenyl)-2-propenylaldehyde,
3-(3-methoxy-4-protectedhydroxyphenyl) propionaldehyde, and
3-(3-methoxy-4-protectedhydroxyphenyl)-2-propenylaldehyde,
and the acetals derived therefrom.

An alcohol derivative is 3-(3-methoxy-4-hydroxyphenyl) propylalcohol.

For a typical example of the case where the material to be purified is in the solution form, the reaction solution, which contains the object compound obtained by conducting the reductive alkylation reaction for producing the object compound described above, is cited. With regard to this solution, the object compound can be purified by making use of a process for crystallizing the object compound described above.

With regard to the material to be purified, which is in the solution form, in case that the reaction solution contains an insoluble material, for example, insoluble catalyst, which exists when catalyst has been used, or the like exists in this solution may be purified, the insoluble material is removed therefrom when necessary. In this case, similarly, the insoluble material can be removed from the solution by filtration or the like.

By subjecting the solution thus obtained to the process for crystallization (using the solvent used for crystallization of the object compound described above.), the object compound can be separated after crystallization. For example, in case of the solvent used for crystallization of the object compound described above, by subjecting the solution to a process for crystallization with concentration, or in a process for substitution of solvent, independent of the fact of whether a solvent in the solution, may contain the solvent used for crystallization of the object compound described above or not, by substituting the solvent used for crystallizing the object compound (the solvent used for crystallization of the object compound), for example, an organic solvent (a singular solvent consisting of one kind of solvent or a mixed solvent consisting of plural solvents) or a mixed solvent of at least one solvent of these organic solvents with water, for the solvent, the object compound can be easily crystallized.

Or, the object compound can be crystallized after extraction with water. For example, as regards the mixture obtained after concentration of said solution, by extracting the object compound with the use of water, or conducting the extraction operation with an organic solvent, which can not be homogeneously mixed with water (plural organic solvents can be used) and water, and forming layers which separate in the solution, whereby the object compound is extracted in the aqueous layer, and further, by substituting an appropriate solvent used for crystallization (the solvent used for crystallization of the object compound described above) for the solvent, for example, by changing the water into the organic solvent(s) or a mixed solvent of the organic solvent(s) with water, the object compound can be crystallized therefrom. When the object compound is extracted with a mixed solvent of water and organic solvent(s) described above, which forms a layer separate from the aqueous layer when mixed with water, firstly, by adding water to the residue or the like, most of the object compound is dissolved in water, and secondly, by adding the organic solvent(s), which forms a layer separate from the aqueous layer, thereto, a mixed solvent forming two layers is prepared, and successively, the object compound can be extracted into the aqueous layer. On the other hand, oppositely, firstly, by adding the organic solvent(s) described above to the residue or the like, most of the impurities are dissolved in this organic solvent(s), and secondly, by adding water thereto, a mixed solvent forming two layers is prepared, and successively, the object compound can be also extracted into the aqueous layer.

In the process for crystallization described above, when impurities, in particular, Aspartame are present, a process for separating such compound in advance is extremely favorable for the process for crystallizing the object compound conducted thereafter. For example, for the process for separating such a compound as described above, a process for separating Aspartame, when an appropriate organic solvent is substituted for the solvent in the solution, such as synthetic reaction solution obtained in the above, by filtrating is cited.

On the other hand, when the material to be purified does not contain a solvent, by selecting concretely an appropriate solvent from the solvent used for crystallization of the object compound described above, and by making use of the crystallization of the object compound using the solvent used for crystallizing the object compound used in the process for crystallization with concentration described above or the process for substitution of solvent described above (the solvent used for crystallization of the object compound) or the crystallization of the object compound after extraction with water for crystallizing the object compound directly, the object compound can be easily purified. In this case, as described above, by previously conducting the process described above for separating impurities, in particular, Aspartame in the case where the material to be purified contains Aspartame, the object compound is also favorably purified.

As described above, for the solvent used for this object compound, preferably, at least one solvent selected from the group consisting of alcohol(s), such as methanol, ethanol, isopropanol and the like, tetrahydrofuran, acetonitrile, toluene, ether, acetone, acetic acid, and acetic acid ester(s), such as ethyl acetate, isopropyl acetate and the like, or a mixed solvent (containing a homogeneous or heterogeneous mixed solvent) of at least one solvent of these organic solvents with water can be used.

When the material to be purified is in solution form, for the solvent, preferably, at least one solvent selected from the group consisting of alcohol(s), such as methanol, ethanol, isopropanol and the like, tetrahydrofuran, acetone, acetonitrile, toluene, ether, acetic acid, and acetic acid ester(s), such as ethyl acetate, isopropyl acetate and the like, or a mixed solvent of at least one solvent of these organic solvents with water (preferable solvent used for crystallization) can be used.

When a solvent, which is different from such solvent, is used, the process for crystallization can be conducted by selecting concretely such preferred solvents used for crystallization from the solvent used for crystallization of the object compound described above.

When the Aspartame described above is present as an impurity material in the material to be purified, efficiently, Aspartame is removed therefrom in advance, and a method for removing it after precipitation can be used. At that time, for the solvent used therefor, at least one solvent (containing a mixed solvent) selected from the group consisting of acetic acid ester(s), such as ethyl acetate, isopropyl acetate and the like, ether, chloroform, dichloromethane (methylene chloride), hexane, toluene, alcohol(s), such as methanol, ethanol, isopropanol and the like, tetrahydrofuran, acetone, acetonitrile, acetic acid and water (hereinafter, "the solvent used for separating Aspartame".) can be cited. Furthermore, with regard to the mixed solvent used here (in the reaction), similarly, a homogeneous solvent is preferably used, and a heterogeneous solvent can be also used.

When conducting the extraction with water described above, the extraction is conducted making use of the distribution with the organic solvent (or organic solvent based solvent) described above, which can not be mixed with water homogeneously, and water. For the organic solvent used in this case, preferably, at least one solvent (including a mixed solvent) selected from the group consisting of acetic acid ester(s), such as ethyl acetate, isopropyl acetate and the like, ether, chloroform, dichloromethane (methylene chloride), hexane, toluene, alcohol(s), such as methanol, ethanol, isopropanol and the like, tetrahydrofuran, acetone, acetonitrile and acetic acid (hereinafter, which may be called "the organic solvent used for extraction with water") can be used. Through such distribution with organic solvent(s) after the extraction with water, the process for crystallization described above is effectively conducted.

(Crystals of the Object Compound)

In the present invention, the object compound is obtained by the method of production or purification described above. In particular, the object compound in the crystalline form is preferred in view of its high purity, and the crystals of the object compound, which show the following physicochemical property: X-ray diffraction peaks in at least diffraction angles of 5.55°, 12.25°, 18.5°, 21.1° and 22.45° (2θ, CuKα ray), is preferred.

When producing these crystals, the crystallization solvent is at least one solvent (containing a mixed solvent) selected from the group consisting of alcohol(s), such as methanol, ethanol, isopropanol and the like, tetrahydrofuran, acetonitrile, toluene, ether, acetone, acetic acid, and acetic acid ester(s), such as ethyl acetate, isopropyl acetate and the like, or a mixed solvent of at least one solvent of these organic solvents with water (the solvent used for crystallization of the object compound described above) are used, and the crystals obtained thereby are more preferred.

As described above, N-[N-[3-(3-methoxy-4-hydroxyphenyl)propyl]-L-α-aspartyl]-L-phenylalanine 1-methyl ester, which is obtained or can be obtained in the present invention, is a compound having an extremely high sweetening potency. Accordingly, the compound is useful as a sweetener.

(Example of Typical Production for the Object Compound)

The following description is that of a typical and more preferred example of production; a process for production in the present invention is explained in detail; and the process for production in the present invention is not limited thereto.

Aspartame and 3-(3-methoxy-4-hydroxyphenyl) propionaldehyde or its derivative is subjected to a reductive alkylation reaction with hydrogen in the presence of a catalyst for hydrogenation, as described above, in an organic solvent, or a mixed solvent of organic solvent(s) with water. The object compound is produced.

As described above, with regard to the derivative of 3-(3-methoxy-4-hydroxyphenyl) propionaldehyde, such is preferably selected from 3-(3-methoxy-4-hydroxyphenyl)-2-propenylaldehyde, 3-(3-methoxy-4-hydroxyphenyl)-2-propionaldehyde, wherein the hydroxyl group is protected with a benzyl group or the like, and 3-(3-methoxy-4-hydroxyphenyl)-2-propenylaldehyde, wherein the hydroxyl group is protected with a benzyl group or the like), and the acetals derived therefrom and the like. Similar to Aspartame, these derivatives can be easily obtained or produced as starting materials. When the object compound is obtained in high purity, considering the cost of Aspartame and the laborious operations for removing Aspartame in a process for purification, the reaction is preferably conducted by using said aldehyde or its derivative in excess. However, even though Aspartame is admixed in the final product, the use of the material as a sweetener is allowable. Accordingly, oppositely, Aspartame can be also used in equimolecular amounts or in excess, according to the purpose of adjusting sweetening potency and the like.

In the reductive alkylation reaction, the organic solvent, which dissolves the starting materials and product, can be used, and more preferably, alcohol(s), such as methanol, ethanol, isopropanol and the like, and further, most preferably in the view of cost, methanol, or a mixed solvent of any such organic solvent(s) with water, and further preferably, a mixed solvent of methanol with water are used. When the mixed solvent of organic solvent(s) with water is used, the composition ratio of both components is not particularly limited, and it is preferred that Aspartame, aldehyde or its derivative and a product as the object compound are dissolved fully in the solvent. Tetrahydrofuran, acetonitrile, acetic acid, and acetic acid ester(s), such as ethyl acetate, isopropyl acetate and the like are used for the solvent except for alcohol(s).

As the catalyst used for the reductive alkylation reaction, the catalyst is selected from general hydrogenation catalyst, such as palladium based catalysts, such as palladium on carbon and the like, platinum based catalysts, such as platinum on carbon and the like, rhodium based catalysts, such as rhodium-alumina and the like, nickel based catalysts, such as Raney nickel and the like, can be used. The amount of catalyst employed is not particularly limited. For example, when 10% palladium on carbon (containing 50% water), is the catalyst, the amount used is within the range of one hundredth to one fourth part ($1/100$ to $1/4$) at the ratio by weight to Aspartame.

The pH of the reaction mixed solution is preferably within the range of about 4.0 to about 6.5, and when the pH is out of this range, the pH of the reaction mixed solution can be adjusted with ordinary acids, such as acetic acid or the like, or ordinary bases, such as sodium hydrogen carbonate, or the like.

When the reaction is conducted under a hydrogen atmosphere and at a pressure of about 0.1 MPa, the reaction goes well enough. The reaction can be also conducted under a hydrogen pressure of about 0.1 to 1.0 MPa.

With regard to the reaction temperature, the reaction proceeds easily at 15 to 30° C. or so, and in order to increase the solubility of reactant, the reaction can be also conducted by increasing the temperature to approximately 50° C. With regard to the reaction time, the reaction may be conducted within a range of 2 to 48 hours. However, the reaction is preferably conducted within a range of about 12 to 16 hours.

In order to remove the insoluble catalyst that has been used, the reaction solution containing the object compound produced may be filtered, and any known method of filtration may be used. A filter aid (an auxiliary agent for filtration), such as celite or the like, may also be used effectively.

The reaction solution described above in which the catalyst has been removed by filtration in such a manner, may be concentrated, allowed to stand or cooled to precipitate crystals. However, in order to crystallize the product in a good yield and at that time obtain highly pure crystals, the operation of removing the by-product is preferably conducted. By substituting a solvent, which only with difficulty dissolves Aspartame, for the reaction solvent, the remaining Aspartame can be effectively removed. For example, by suspending the reaction product in ethyl acetate and adding methanol in an amount which is one tenth to one twentieth part ($1/10$ to $1/20$) of the amount of ethyl acetate thereto, only Aspartame is precipitated after the solution becomes homogeneous. And, by separating the Aspartame by filtration, most of the residual Aspartame can be removed. With regard to the solvent which can be used in this operation, at least one solvent (a homogeneous or heterogeneous mixed solvent) selected from the group consisting of acetic acid ester(s), such as ethyl acetate, isopropyl acetate and the like, ether, chloroform, dichloromethane (methylene chloride), hexane, toluene, alcohol(s), such as methanol, ethanol, isopropanol and the like, tetrahydrofuran, acetone, acetonitrile, acetic acid and water is employed. Further, among the solvents, a solvent, which has a selectively low solubility for Aspartame, is especially preferred.

On the other hand, when the reaction filtrate obtained as described above is concentrated, the object compound does not crystallized therefrom, upon substitution of organic solvent(s) or a mixed solvent of the organic solvent(s) with water (the solvent used for crystallization of the object compound) for the solvent therein, and the objective of crystallization can be realized. For example, by substituting ethyl acetate for the reaction solvent, and further, adding a small amount of methanol thereto, the object compound is easily obtained as crystals. Further, since fat-soluble by-product dissolves in the mother liquor, when the crystals of the object compound are filtered and washed, high purity object compound is obtained. For this crystallization, the solvent used is as described. For example, preferably, the organic solvent, which is at least one organic solvent selected from the group consisting of alcohol(s), such as methanol, ethanol, isopropanol and the like, tetrahydrofuran, acetonitrile, toluene, ether, acetone, acetic acid, and acetic acid ester(s), such as ethyl acetate, isopropyl acetate and the like, or a mixed solvent of at least one solvent of these organic solvents with water (containing a homogeneous or heterogeneous mixed solvent) can be used.

When the solvent which has been used in the synthesis reaction of the object compound corresponds to the solvent used for crystallization of the object compound as described above, the object compound can also be crystallized by subjecting the synthetic reaction solution in itself to a process for crystallization directly. However, because of reaction yield, the mixed state of impurities and the like, in most instances, the crystallization is difficult. In this event, by adjusting the rate of mixture of plural mixed solvents, or by changing the solvent to another kind of solvent in order to subject the object compound to two steps of crystallization, the efficiency of crystallization can be further improved.

For example, when the reaction has been conducted in a methanol or methanol-water system, conversion of solvent therein to ethyl acetate-methanol is preferred. In this instance, a portion of methanol which has been used in the reaction can be used as the methanol for crystallization. However, because a catalyst is used, in the event water is removed therefrom as much as possible after the reaction, the methanol present is mostly removed along with water. In this case, methanol can be further added separately thereto and used. Furthermore, a small portion of water may be added thereto.

As a technique for effectively removing a reaction by-product, the process of extraction with water can be employed. In this instance, the reaction mixture can be distributed in an organic solvent, which can not be homogeneously mixed with water, and water, and the object compound is then extracted into the aqueous layer and the by-product into the organic solvent. For example, when the reaction mixture is distributed into ethyl acetate and water, very little of the residual aldehyde derivative and the by-product are present in the aqueous layer. In this distribution operation, the organic solvent is at least one organic solvent (containing a mixed solvent) selected from the group consisting of acetic acid ester(s), such as ethyl acetate, isopropyl acetate and the like, ether, chloroform, dichloromethane (methylene chloride), hexane, toluene, alcohol(s), such as methanol, ethanol, isopropanol and the like, tetrahydrofuran, acetone, acetonitrile and acetic acid.

The object compound obtained by the process for extraction by the above described distribution operation, which is subjected to a concentration operation under reduced pressure or the like to remove water therefrom, can be crystallized from the above crystallization solvent (the solvent used for crystallization of the object compound), namely, which is at least one organic solvent selected from the group consisting of alcohol(s), such as methanol, ethanol, isopropanol and the like, tetrahydrofuran, acetonitrile, toluene, ether, acetone, acetic acid and acetic acid ester(s), such as ethyl acetate, isopropyl acetate and the like, or a mixed solvent of at least one solvent selected from these organic solvents with water.

(Example of Typical Purification of the Object Compound)

Hereinafter, a method for purification in the present invention is described.

The method is directed to a method for purifying the object compound, which comprises the steps of subjecting the object compound containing at least one of Aspartame, a peptide derivative, an amino acid, an amino acid derivative, an aldehyde, an acetal or an alcohol derivative as an impurity to a process comprising at least any one of the following methods:
 a. crystallization with a solvent used for crystallization, such as crystallization with concentration, crystallization with substitution of solvent and the like;
 b. crystallization after extraction with water; and
 c. in the event Aspartame is present, crystallization after a process for separating Aspartame;
to crystallize said compound.

The solvent for crystallization is a solvent that dissolves the object compound described above and the impurities described above, and characteristically for the solvent, it is selected from the solvents used for crystallization of the object compound described above.

With respect to the matter of a method of crystallization with the solvent used for crystallization as such, crystallization can be conducted making use of a known method therefor. For example, a method is known in which crystallization occurs with concentration. Methods having various steps of crystallization with concentration are known and can be used. A convenient method is to use the organic solvent, which has been used for the reductive alkylation reaction in the production of the object compound described above, as the solvent for crystallization.

With regard to the solvent used for crystallization, as explained above, preferably, at least one organic solvent selected from the group consisting of alcohol(s), such as methanol, ethanol, isopropanol and the like, tetrahydrofuran, acetonitrile, toluene, ether, acetone, acetic acid, and acetic acid ester(s), such as ethyl acetate, isopropyl acetate and the like, or a mixed solvent of at least one solvent of these organic solvents with water, more preferably, alcohol(s), and further, most preferably in the view of cost, methanol, or a mixed solvent of any such organic solvent(s) with water, and further, preferably, alcohol(s) (such as methanol, ethanol, isopropanol and the like), in particular, a mixed solvent of methanol with water are used. In the event a mixed solvent of organic solvent(s) with water is used, the composition ratio of both components is not particularly limited, and it is preferred that the impurities contained therein, for example, Aspartame, aldehyde, alcohol derivatives, derivatives thereof, and the like, and the object compound are dissolved completely in the solvent. Tetrahydrofuran, acetone, acetonitrile, acetic acid and acetic acid ester(s) (such as ethyl acetate, isopropyl acetate and the like) are cited for the solvent except alcohol(s).

With respect to the matter of a detailed explanation of the solvent used for crystallization of an object compound, as a matter of course, the contents explained on the solvent used for crystallization of the object compound described above are literally applied thereto.

Furthermore, with respect to the product of the reductive alkylation reaction described above, this method for purification can be applied thereto. However, in the case the solvent used for crystallization contains impurities, for example, in order to remove insoluble catalyst which has been used for the synthesis reaction, the solution form of solvent containing the object compound, for example, the reaction solution described above may be filtered. At that time, any ordinary method for filtration may be used. A filter aid, such as celite or the like, is also used effectively.

In the event the purification operation is conducted with the solution thus obtained, for example, the reaction solution, wherein the catalyst has been removed by filtration, it may be concentrated, and allowed to stand or to cool to precipitate crystals. However, in order to crystallize the compound in a good yield and thereby obtain high pure crystals, preferably the operation which removes the impurities, such as the by-product in the synthesis reaction solution employed, is conducted in advance. In the event Aspartame (part or most) is removed by a separation operation in advance, by substitution with a solvent, which only dissolves Aspartame with difficulty (the organic solvent used for removing Aspartame described above), for the solvent used for crystallization, the residual Aspartame and the like can be effectively removed. For example, in the event the material to be purified, synthetic reaction product or the like is used, by suspending the reaction product in ethyl acetate and adding methanol in the amount which is one tenth to one twentieth part ($\frac{1}{10}$ to $\frac{1}{20}$) of amount of ethyl acetate, only Aspartame is precipitated after the solution becomes homogeneous. And, by removing the Aspartame by filtration, most of the residual Aspartame can be removed. With respect to the solvent which is used in this operation, at least one solvent (or a mixed solvent) selected from the group consisting of acetic acid ester(s), such as ethyl acetate, isopropyl acetate and the like, ether, chloroform, dichloromethane (methylene chloride), hexane, toluene, alcohol(s), such as methanol, ethanol, isopropanol and the like, tetrahydrofuran, acetone, acetonitrile, acetic acid and water is used. Further, among the solvents, the solvent which has a selectively low solubility for Aspartame which is to be removed is especially preferred.

Thus, in case when the solution containing the material to be purified is concentrated, the object compound is not crystallized therefrom, by substituting an organic solvent or a mixed solvent of the organic solvent(s) with water for the solvent therein, the object for crystallization can be executed. For example, by substituting ethyl acetate for the reaction solvent, and further, adding a small amount of methanol thereto, the object compound is easily obtained as crystals. Further, since fat-soluble by-product is dissolved in mother liquor, when the crystals of the object compound are filtered and washed, a high purity object compound can be obtained. For this crystallization, the solvent used for crystallization of the object compound described above is used. For example, preferably, the organic solvent which is at least one solvent selected from the group consisting of alcohol(s), such as methanol, ethanol, isopropanol and the like, tetrahydrofuran, acetone, acetonitrile, toluene, ether, acetic acid and acetic acid ester(s), such as ethyl acetate, isopropyl acetate and the like, or a mixed solvent of at least one solvent of these organic solvents with water (containing a homogeneous or heterogeneous mixed solvent) can be used.

With regard to a method for effectually removing the impurity admixed, for example, in the case the synthetic reaction solution described above is applied, the reaction by-product, a method in which the reaction mixture is distributed in an organic solvent can be used, which can not be mixed with water homogeneously, and water, and extracting the object compound into the aqueous layer and the impurity, for example, the by-product, in the organic solvent. For example, when the reaction mixture described above is distributed in ethyl acetate and water, very little of the residual aldehyde derivative and the by-product are present in the aqueous layer. In this distribution operation, as the organic solvent, as least one organic solvent selected from the group consisting of acetic acid ester(s), such as ethyl acetate, isopropyl acetate and the like, ether, chloroform, dichloromethane (methylene chloride), hexane, toluene, alcohol(s), such as methanol, ethanol, isopropanol and the like, tetrahydrofuran, acetone, acetonitrile, and acetic acid, or a mixed organic solvent of these plural organic solvents, can be used.

The object compound obtained in the process for extraction through the above distribution operation, which is subjected to concentration under reduced pressure or the like to remove water therefrom, can be crystallized by using the above solvent which has been used for crystallization of the object compound in the present invention; that is, a solvent selected from the group consisting of alcohol(s), such as methanol, ethanol, isopropanol and the like, tetrahydrofuran, acetone, acetonitrile, toluene, ether, acetic acid and acetic acid ester(s), such as ethyl acetate, isopropyl acetate and the like, and a mixed organic solvent of these solvents, and a mixed solvent of any such organic solvent(s) with water (containing a homogeneous or heterogeneous mixed solvent).

(Sweetener and the Other Products Using (Containing) the Object Compound)

The object compound obtained in the present invention, particularly in crystalline form, can be used as a sweetener. In this case, the sweetener can be employed in combination with a carrier, a bulking agent, an excipient or other components which are necessary for sweeteners. With respect to a method which uses the components, such as a kind of those, the amount used of those and the like, the known components or components that will develop in the future, which can be used for such components, can be suitably mixed by making use of a method for mixing the components, which is known per se. At that time, the other sweetener(s) and component(s) giving a sweet taste thereto can be used in combination therewith.

The object compound in the present invention, particularly in crystalline form, can be used by addition to the products in need of a sweet taste with the intention of imparting a sweet taste thereto. Such a method is also within the scope of the present invention. At that time, as a matter of course, a carrier, a bulking agent, an excipient, other components necessary for sweeteners, other sweetener components, which are described above, and the like, similar to the sweetener described above, can be used in combination therewith.

In addition to the sweetener, product(s) in need of a sweet taste such as, for example, drinks, food, confectionary, for example, chewing gum, medicaments, products used in zoological applications and the like, containing the object compound are within the scope of the invention. Also within the scope of the invention are methods of adding the object compound to products in need of a sweet taste. Methods for use of the object compound can be conducted by making use of known method for use of sweeteners and components which impart a sweet taste to various materials.

Having generally described this invention, a further understanding can be obtained by reference to certain specific examples which are provided herein for purposes of illustration only and are not intended to be limiting unless otherwise specified.

EXAMPLES

Example 1

Production of N-[N-[3-(3-methoxy-4-hydroxyphenyl)propyl]-L-α-aspartyl]-L-phenylalanine 1-methyl Ester and Purification of the Same, and Separation of Crystals thereof A 8.83 g (30.0 mmol) amount of Aspartame (APM) and 6.89 g (38.3 mmol) of 3-(3-methoxy-4-hydroxyphenyl) propionaldehyde were added to methanol 150 ml, and the mixture was stirred briefly. A 2.65 g amount of 10% palladium on carbon (containing 50% water) was added to this slurry, and the mixed product was stirred under a hydrogen atmosphere of atmospheric pressure (0.1 MPa) at room temperature for 40 hours. The catalyst was removed from the reaction solution by filtering, and then the catalyst was washed with methanol. When the filtrate was mixed with the wash solution, and the mixture was analyzed by HPLC (high performance liquid chromatography), 9.05 g (19.7 mmol, 65.8%) of the titled object compound had been produced. The amount of residual Aspartame was not more than 0.5% of the object compound as determined from the ratio of peak areas of HPLC chromatogram.

After the reaction solution was concentrated under reduced pressure, the residue was dissolved in 50 ml of ethyl acetate, and moreover, 5 ml of methanol was added to the mixture. When the mixture was allowed to stand, crystals of N-[N-[3-(3-methoxy-4-hydroxyphenyl)propyl]-L-α-aspartyl]-L-phenylalanine 1-methyl ester were precipitated therefrom. The crystals were collected by filtering, washed with a small amount of ethyl acetate and dried under reduced pressure. After these crystals were dissolved in 20 ml of methanol, the mixture was concentrated to half as much. The crystallization proceeded from the oil-like part as 20 ml of water was added gradually to the remaining residue (mixture thus concentrated). The crystals thus precipitated and separated therefrom were filtered after breaking-up and the product was washed with a small amount of mixed solvent of methanol and water, and the product was dried under reduced pressure to obtain 5.76 g (12.6 mmol) of the title compound. When the compound was analyzed by HPLC, the purity of the same was not less than 99%.

Above mother liquor obtained by recrystallization with ethyl acetate-methanol was extracted with water 50 ml twice, and successively the aqueous layer obtained was concentrated under reduced pressure. Similar to the above, the remaining residue was crystallized from methanol-water, and 0.48 g (1.05 mmol) of the title of object compound were obtained. When the compound was determined by HPLC, the purity of the same was not less than 99%.

Example 2

Production of N-[N-[3-(3-methoxy-4-hydroxyphenyl) propyl]-L-α-aspartyl]-L-phenylalanine 1-methyl Ester and Purification of the Same, and a Separation of Crystals thereof A 736 mg (2.5 mmol) amount of Aspartame and 535 mg (3.0 mmol) of 3-(3-methoxy-4-hydroxyphenyl)-2-propenylaldehyde were suspended in 15 ml of methanol, and 200 mg of 10% palladium on carbon (containing 50% water) was added to the slurry thus obtained. After the reaction solution was reacted under hydrogen atmosphere at atmospheric pressure at room temperature for 16 hours, the catalyst was removed from the reaction solution by filtering, and further, the catalyst was washed with methanol.

The reaction solution was concentrated under reduced pressure, and 20 ml of ethyl acetate and 2 ml of methanol were added thereto. The solution became homogeneous once, and Aspartame began to precipitate after a short time. Further, after 10 ml of ethyl acetate was added to the mixture, and the mixture was stirred briefly, the insoluble materials were removed by filtration. The filtrate was concentrated under reduced pressure to an amount of half as much, and the mixture was extracted with 30 ml of water twice. After the aqueous layer was concentrated under reduced pressure, 2 ml of methanol were added to the residue, and further, when 10 ml of water was added to the mixture gradually, the crystals precipitated therefrom.

The crystals thus precipitated and separated were collected by filtration after breaking-up, and the product was washed with a small amount of mixed solvent of water and methanol, and the product was dried under reduced pressure, with the result that 280 mg (0.61 mmol) of N-[N-[3-(3-methoxy-4-hydroxyphenyl)propyl]-L-α-aspartyl]-L-phenylalanine 1-methyl ester was obtained. (The purity of the product was not less than 97% as determined by HPLC.)

Example 3

Production of N-[N-[3-(3-methoxy-4-hydroxyphenyl) propyl]-L-α-aspartyl]-L-phenylalanine 1-methyl Ester A 500 mg (1.70 mmol) amount of Aspartame and 306 mg (1.70 mmol) of 3-(3-methoxy-4-hydroxyphenyl) propionaldehyde were suspended in 9 ml of methanol, and 100 mg of 10% palladium on carbon (containing 50% water) was added to the mixture. The mixture was stirred under hydrogen atmosphere at atmospheric pressure at room temperature for 16 hours. The catalyst was removed by filtration, and further washed with methanol. When the filtrate and the wash solution were analyzed by HPLC, 71.0% of the title compound were produced.

Example 4

Production of N-[N-[3-(3-methoxy-4-hydroxyphenyl) propyl]-L-α-aspartyl]-L-phenylalanine 1-methyl ester The reaction of Example 3 was repeated except that 200 mg of 10% palladium on carbon was used as catalyst without changing any other of the reaction conditions of Example 3. Similar to Example 3, when the reaction solution prepared (filtrate and wash solution) was subjected to analysis by HPLC, 73.4% of the title compound was produced.

Example 5

Production of N-[N-[3-(3-methoxy-4-hydroxyphenyl) propyl]-L-α-aspartyl]-L-phenylalanine 1-methyl ester A reaction the same as that of Example 3 was repeated except that 3-(3-methoxy-4-hydroxyphenyl)-2-propenylaldehyde was used in place of 3-(3-methoxy-4-hydroxyphenyl) propionaldehyde without changing any of the other reaction conditions of Example 3. Similar to Example 3, when the reaction solution obtained was subjected to analysis by HPLC, 49.1% of the title compound was produced.

Example 6

Production of N-[N-[3-(3-methoxy-4-hydroxyphenyl) propyl]-L-α-aspartyl]-L-phenylalanine 1-methyl ester A reaction the same as that in Example 3 was repeated except that 3-(3-methoxy-4-benzyloxyphenyl) propionaldehyde was used in place of 3-(3-methoxy-4-hydroxyphenyl)-propionaldehyde without changing any other reaction conditions of Example 3. Similar to Example 3, when the reaction solution prepared was subjected to analysis by HPLC, 60.3% of the title compound was produced.

Example 7

Production of N-[N-[3-(3-methoxy-4-hydroxyphenyl) propyl]-L-α-aspartyl]-L-phenylalanine 1-methyl ester A reaction the same as that of Example 3 was conducted except that 3-(3-methoxy-4-benzyloxyphenyl)-2-propenylaldehyde was used in place of 3-(3-methoxy-4-hydroxyphenyl) propionaldehyde without changing any other reaction conditions of Example 3. Similar to Example 3, when the reaction solution prepared was subjected to analysis by HPLC, 30.2% of the title compound was produced.

Example 8

Production of N-[N-[3-(3-methoxy-4-hydroxyphenyl) propyl]-L-α-aspartyl]-L-phenylalanine 1-methyl ester A reaction the same as that of Example 3 was repeated except that a mixed solvent of 6.75 ml of methanol and 2.25 ml of water, was used in place of methanol without changing any other reaction conditions of Example 3. Similar to Example 3, when the reaction solution prepared was subjected to analysis by HPLC, 58.1% of the title compound was produced.

Example 9

Production of N-[N-[3-(3-methoxy-4-hydroxyphenyl) propyl]-L-α-aspartyl]-L-phenylalanine 1-methyl ester A reaction the same as that of Example 3 was conducted except that a mixed solvent of 6.75 ml of methanol and 2.25 ml of 0.1 M acetic acid aqueous solution, was used in place of methanol without changing any other reaction conditions of Example 3. Similar to Example 3, when the reaction solution prepared was subjected to analysis by HPLC, 50.7% of the title of compound was produced.

Example 10

Production of N-[N-[3-(3-methoxy-4-hydroxyphenyl) propyl]-L-α-aspartyl]-L-phenylalanine 1-methyl ester A reaction the same as that of Example 3 was repeated except that a mixed solvent of 4.5 ml of ethyl acetate and 4.5 ml of water, was used in place of methanol without changing any other reaction conditions of Example 3. Similar to Example 3, when the reaction solution prepared was subjected to analysis by HPLC, 29.4% of the title of compound was produced.

Example 11

Production of N-[N-[3-(3-methoxy-4-hydroxyphenyl) propyl]-L-α-aspartyl]-L-phenylalanine 1-methyl ester A reaction the same as that of Example 3 was repeated except that a hydrogen pressure of 1.0 MPa was employed in place of hydrogen at atmospheric pressure without changing any other reaction conditions of Example 3. Similar to Example 3, when the reaction solution obtained was subjected to analysis by HPLC, 66.6% of the title compound was produced.

Example 12

Production of N-[N-[3-(3-methoxy-4-hydroxyphenyl) propyl]-L-α-aspartyl]-L-phenylalanine 1-methyl ester A reaction the same as that of Example 3 was repeated except that the temperature of the reaction was 50° C. was employed instead of room temperature and the reaction was conducted for 6 hours without changing any other reaction conditions of Example 3. Similar to Example 3, when the reaction solution prepared was subjected to analysis by HPLC, 41.3% of the title compound was produced.

Example 13

Production of N-[N-[3-(3-methoxy-4-hydroxyphenyl) propyl]-L-α-aspartyl]-L-phenylalanine 1-methyl ester A reaction the same as that of Example 5 was repeated except that 200 mg of 5% rhodium on alumina was used instead of 10% palladium on carbon as catalyst for the reductive alkylation without changing any other reaction conditions of Example 5. Similar to Example 5, when the reaction solution obtained was subjected to analysis by HPLC, 32.5% of the title of compound was produced.

Example 14

Production of N-[N-[3-(3-methoxy-4-hydroxyphenyl) propyl]-L-α-aspartyl]-L-phenylalanine 1-methyl ester A reaction the same as that of Example 5 was repeated except that 100 mg of 5% platinum on carbon was used instead of 10% palladium on carbon as catalyst for the reductive alkylation and the reaction was conducted for 2 hours without changing any other reaction conditions of Example 5. Similar to Example 5, when the reaction solution obtained was subjected to analysis by HPLC, 11.8% of the title compound was produced.

Example 15

Production of N-[N-[3-(3-methoxy-4-hydroxyphenyl) propyl]-L-α-aspartyl]-L-phenylalanine 1-methyl ester A 535 mg (3.0 mmol) amount of 3-(3-methoxy-4-hydroxyphenyl)-2-propenylaldehyde and 200 mg of 5% rhodium on alumina was added to methanol 15 ml, and the mixture was reacted under hydrogen atmosphere at atmospheric pressure at room temperature for 2 hours. 736 mg (2.5 mmol) of Aspartame and 150 mg of 10% palladium on carbon (containing 50% water) were added to this mixture, and the reaction was conducted under hydrogen atmosphere at atmospheric pressure at room temperature for 16 hours again. When the reaction solution wherein the catalyst had been removed by filtration was subjected to analysis by HPLC, 57.0% of the title compound was produced.

Example 16

Physico-Chemical Properties on Crystals of N-[N-[3-(3-methoxy-4-hydroxyphenyl) propyl]-L-α-aspartyl]-L-phenylalanine 1-methyl ester The physico-chemical properties on the title compound obtained in Example 1 were as follows.

Mass Spectrometry

ESI-MS (electro spray ionization mass spectrometry) 459.3 (MH$^+$).

Measurement instrument: Thermo Quest TSQ700.
$^1$HNMR (DMSO-d$_6$, 300 MHz) δ: 1.50 to 1.62 (m, 2H), 2.15 to 2.47 (m, 6H), 2.93 (dd, 1H), 3.06 (dd, 1H), 3.37 to 3.43 (m, 1H), 3.62 (s, 3H), 3.74 (s, 3H), 4.53 to 4.61 (m, 1H), 6.53 (dd, 1H), 6.66 (d, 1H), 6.71 (s, 1H), 7.15 to 7.29 (m, 5H), 8.52(d, 1H).

Measurement instrument: Varian Gemini-300.

Melting Point: 158.6° C.

Measurement instrument: MICRO MELTING POINT APPARATUS, manufactured by Yanaco Co.

Optical Rotation $[α]_D^{25}$=−43.4° (c=2, Methanol)

Measurement instrument: DIP-370 Degital Polarimeter, manufactured by JASCO ENGINEERING Co.

IR spectrum (KBr) cm$^{-1}$: 3513, 3336 (NH), 1736 (COOCH$_3$), 1658 (CONH), 1632, 1450 (COO$^-$), 1545, 1520, 1461, 1368, 1350 (CH), 1336, 1319 1276 (CH), 1257, 1230, 1203, 1171, 1125, 1030, 702, 627 (CH).

Measurement instrument: FT-IR Spectrometer PARAGON 1000, manufactured by PERKIN ELMER Co.

Powder X-Ray (CuKα Ray) Analysis: Results are Shown in FIG. 1.

Measurement instrument: PW3050, manufactured by Phillips Co.

Furthermore, similar to Aspartame, the high purity of crystals of compound obtained in the Examples above can be used as a sweetener with a carrier, a bulking agent, an excipient and/or the like conventionally used with sweeteners, where necessary and can be used for foods and the like to be sweetened, by an ordinary method.

EFFECT OF INVENTION

From the discussion above, it is clear that the present invention provides a method of easily producing the present object compound of high purity. Further, the object compound can be efficiently separated by crystallization after subjecting Aspartame and 3-(3-methoxy-4-hydroxyphenyl) propionaldehyde or derivatives thereof to a reductive alkylation reaction in a solvent, and in particular, thereby effectively forming N-[N-[3-(3-methoxy-4-hydroxyphenyl) propyl]-L-α-aspartyl]-L-phenylalanine 1-methyl ester, which is the object compound, in the reaction solvent described above.

Another aspect of the method for purification of the present invention is that the impurity contained in the object compound is effectively separated, and thereby the object compound can be effectively separated after its crystallization. The method for producing the object compound in the present invention as described above is an excellent method for purification when applied to the synthetic reaction solution used at the time when an object compound high purity of is obtained thereby, and the object compound can be effectively crystallized. As a result, in the method for production in the present invention, the synthesis reaction by reductive alkylation can be satisfactorily conducted on an industrial scale, and the object compound described above can be industrially and favorably produced in high purity and in crystalline form from the reaction mixture thus obtained.

In addition, the object compound in crystalline form obtained as described above can be used as a sweetener, and can be used stably, and therefore can be used as a sweetener for foods and drinks and the like.

The disclosure of Japanese priority application 11-253498 filed Sep. 7, 1999 and the disclosure of PCT International Application No. PCT/JP00/05665 filed Aug. 23, 2000 is hereby incorporated by reference into the present application.

Obviously, numerous modifications and variations of the present invention are possible in light of the above teach-

What is claimed as new and is intended to be secured by Letters Patent is:

1. A method for producing N-[N-[3-(3-methoxy-4-hydroxyphenyl)propyl]-L-α-aspartyl]-L-phenylalanine 1-methyl ester, comprising: subjecting N-L-α-aspartyl-L-phenylalanine 1-methyl ester and 3-(3-methoxy-4-hydroxyphenyl) propionaldehyde or a derivatives thereof to reductive alkylation in a solvent to obtain N-[N-[3-(3-methoxy-4-hydroxyphenyl)propyl]-L-α-aspartyl]-L-phenylalanine 1-methyl ester; and (2) crystallizing said N-[N-[3-(3-methoxy-4-hydroxyphenyl)propyl]-L-α-aspartyl]-L-phenylalanine 1-methyl ester wherein said reductive alkylation comprises catalytic hidrogenation, and wherein said derivative thereof is selected from the group consisting of
3-(3-methoxy-4-hydroxyphenyl)-2-propenylaldehyde
3-(3-methoxy-4-protected-hydroxyphenyl) propionaldehyde,
3-(3-methoxy-4-protected-hydroxyphenyl)-2-propenylaldehyde, and
acetals derived therefrom.

2. The method of claim 1, wherein said crystallizing said N-[N-[3-(3-methoxy-4-hydroxyphenyl)propyl]-L-α-aspartyl]-L-phenylalanine 1-methyl ester comprises any one of the following crystallization methods:
a. crystallization with a solvent useful for crystallization;
b. crystallization after extraction with water; and
c. crystallization after separation N-L-α-aspartyl-L-phenylalanine 1-methyl ester.

3. The method of claim 1, wherein said solvent for said reductive alkylation reaction is at least one solvent selected from the group consisting of alcohols, tetrahydrofuran, acetonitrile, toluene, acetic acid and acetic acid esters, and mixed solvent which comprise at least one of these organic solvents and water.

4. The method of claim 2, wherein said N-[N-[3-(3-methoxy-4-hydroxyphenyl)propyl]-L-α-aspartyl]-L-phenylalanine 1-methyl ester is crystallized by a process of concentration or by a process for solvent substitution.

5. The method of claim 1, wherein said solvent for said crystallization of said N-[N-[3-(3-methoxy-4-hydroxyphenyl)propyl]-L-α-aspartyl]-L-phenylalanine 1-methyl ester at least one solvent selected from the group consisting of alcohols, tetrahydrofuran, acetonitrile, toluene, ether, acetone, acetic acid, acetic acid esters, and mixed solvent which comprise at least one of these organic solvents and water.

6. The method of claim 1, wherein said solvent for said crystallization of said N-[N-[3-(3-methoxy-4-hydroxyphenyl)propyl]-L-α-aspartyl]-L-phenylalanine 1-methyl ester is the same solvent which has been used in the reductive alkylation reaction.

7. The method of claim 4, wherein said N-[N-[3-(3-methoxy-4-hydroxyphenyl)propyl]-L-α-aspartyl]-L-phenylalanine 1-methyl ester is crystallized by solvent substitution using at least one solvent selected from the group consisting of alcohols, tetrahydrofuran, acetonitrile, toluene, ether, acetone, acetic acid, acetic acid esters, and mixed solvents which comprise at least one of these organic solvents and water.

8. The method of claim 1, wherein said solvent of the said reductive alkylation reaction is one or more alcohols or a mixed solvent of one or more alcohols and water, and the solvent of said crystallization of said N-[N-[3-(3-methoxy-4-hydroxyphenyl)propyl]-L-α-aspartyl]-L-phenylalanine 1-methyl ester is one or more alcohols or a mixed solvent comprising one or more alcohols.

9. The method of claim 2, wherein said N-[N-[3-(3-methoxy-4-hydroxyphenyl)propyl]-L-α-aspartyl]-L-phenylalanine 1-methyl ester is crystallization after extraction with water using at least one solvent selected from the group consisting of alcohols, tetrahydrofuran, acetonitrile, toluene, ether, acetone, acetic acid, acetic acid esters, and mixed solvent which comprise at least one of these organic solvents and water.

10. The method of claim 2, wherein said N-[N-[3-(3-methoxy-4-hydroxyphenyl)propyl]-L-α-aspartyl]-L-phenylalanine 1-methyl ester is crystallized after extraction with water and said extraction with water is conducted with a mixed solvent which comprises water and one or more organic solvents, wherein said organic solvent forms a layer which separates from an aqueous layer upon mixture with water, and said N-[N-[3-(3-methoxy-4-hydroxyphenyl)propyl]-L-α-aspartyl]-L-phenylalanine 1-methyl ester is extracted into the aqueous layer.

11. The method of claim 10, wherein said organic solvent is at least one solvent selected from the group consisting of acetic acid esters, ether, chloroform, dichloromethane, hexane, toluene, alcohols, tetrahydrofuran, acetone, acetonitrile and acetic acid.

12. The method of claim 2, wherein said N-[N-[3-(3-methoxy-4-hydroxyphenyl)propyl]-L-α-aspartyl]-L-phenylalanine 1-methyl ester is crystalled after having separated N-L-α-aspartyl-L-phenylalanine 1-methyl ester and is crystallized from at least one solvent selected from the group consisting of alcohols, tetrahydrofuran, acetonitrile, toluene, ether, acetone, acetic acid, acetic acid esters, and mixed solvent which comprise at least one of these organic solvents and water.

13. The method of claim 2, wherein said process for separating N-L-α-aspartyl-L-phenylalanine 1-methyl ester is a process for separating N-L-α-aspartyl-L-phenylalanine 1-methyl ester by crystallization or precipitation with at least one solvent selected from the group consisting of acetic acid esters, ether, chloroform, dichloromethane, hexane, toluene, alcohols, tetrahydrofuran, acetone, acetonitrile, acetic acid and water.

14. The method of claim 1, wherein said reductive alkylation reaction is conducted in at least one organic solvent which dissolves the starting materials or a mixed solvent of said organic solvents and water, and when an insoluble material is present in the reaction mixture obtained after said reductive alkylation reaction, said insoluble material is separated by filtration.

15. The method of claim 1, wherein said catalytic hydrogenation is conducted in the presence of at least one catalyst selected from the group consisting of palladium, platinum, and rhodium based catalysts.

16. The method of claim 1, wherein said catalytic hydrogenation is conducted at a hydrogen pressure of 0.1 to 1 MPa.

17. The method of claim 1, wherein said reductive alkylation reaction is conducted at a temperature ranges from 15 to 50° C., and the reaction time of from 2 to 48 hours.

18. The method of claim 1, wherein said reductive alkylation reaction is carried out in reaction solvent having a pH of from 4 to 6.5.

19. The method of claim 1, wherein the molar ratio of said N-L-α-aspartyl-L-phenylalanine 1-methyl ester to said 3-(3-methoxy-4-hydroxyphenyl)propionaldehyde or derivative thereof ranges from 0.5 to 2.

20. The method of claim 1, wherein said 3-(3-methoxy-4-hydroxyphenyl)propionaldehyde or derivative thereof is prepared by subjecting 3-(3-methoxy-4-hydroxyphenyl)-2-propenylaldehyde or acetal thereof, wherein the hydroxyl group may be protected, to reduction to obtain said 3-(3-methoxy-4-hydroxyphenyl)-2-propenylaldehyde or derivative thereof.

21. The method of claim 20, wherein said reduction is conducted in the presence of a reduction catalyst or a rhodium based catalyst.

22. The method of claim 2, wherein said crystallization of said N-[N-[3-(3-methoxy-4-hydroxyphenyl)propyl]-L-α-aspartyl]-L-phenylalanine 1-methyl ester is carried out in the same solvent which has been used in the reductive alkylation reaction.

23. The method of claim 2, wherein said solvent of the reductive alkylation reaction is one or more alcohols or a mixed solvent of one or more alcohols and water, and the solvent of the crystallization of said N-[N-[3-(3-methoxy-4-hydroxyphenyl)propyl]-L-α-aspartyl]-L-phenylalanine 1-methyl ester is one or more alcohols or a mixed solvent comprising one or more alcohols.

* * * * *